US012594177B2

(12) United States Patent
Kuehl et al.

(10) Patent No.: US 12,594,177 B2
(45) Date of Patent: Apr. 7, 2026

(54) ANKLE BRACE

(71) Applicant: MUELLER SPORTS MEDICINE, INC., Prairie du Sac, WI (US)

(72) Inventors: Sarah Kuehl, Madison, WI (US); Kayla Daken, Prairie du Sac, WI (US)

(73) Assignee: MUELLER SPORTS MEDICINE, INC., Prairie du Sac, WI (US)

( * ) Notice: Subject to any disclaimer, the term of this patent is extended or adjusted under 35 U.S.C. 154(b) by 203 days.

(21) Appl. No.: 18/213,871

(22) Filed: Jun. 25, 2023

(65) Prior Publication Data

US 2023/0414394 A1      Dec. 28, 2023

Related U.S. Application Data

(60) Provisional application No. 63/355,997, filed on Jun. 27, 2022.

(51) Int. Cl.
A61F 5/01          (2006.01)
A61F 5/058         (2006.01)

(52) U.S. Cl.
CPC .......... A61F 5/0111 (2013.01); A61F 5/0585 (2013.01)

(58) Field of Classification Search
CPC ......... A61F 5/0111; A61F 5/0585; A61F 5/14
See application file for complete search history.

(56) References Cited

U.S. PATENT DOCUMENTS

| | | | | |
|---|---|---|---|---|
| 5,038,762 A | * | 8/1991 | Hess ..................... | A43B 7/1495 |
| | | | | 602/27 |
| 5,897,515 A | * | 4/1999 | Willner ................. | A61F 5/0111 |
| | | | | 602/6 |
| 6,447,469 B1 | * | 9/2002 | Ritchie ................. | A61F 5/0111 |
| | | | | 602/65 |
| 9,522,075 B1 | * | 12/2016 | Ritchie ................. | A61F 5/0102 |
| 10,213,330 B2 | * | 2/2019 | Causse ..................... | A43B 7/14 |
| 2002/0077576 A1 | * | 6/2002 | Saraceni ............... | A61F 5/0111 |
| | | | | 602/23 |
| 2007/0038169 A1 | * | 2/2007 | Alon ..................... | A61F 5/0111 |
| | | | | 602/27 |
| 2009/0192428 A1 | * | 7/2009 | Deboer ................. | A61F 13/065 |
| | | | | 602/65 |
| 2019/0269543 A1 | * | 9/2019 | Hsu ....................... | A61F 5/0585 |

* cited by examiner

*Primary Examiner* — Keri J Nelson

(74) *Attorney, Agent, or Firm* — Casimir Jones, S.C.; Rick L. Abegglen

(57)                ABSTRACT

An ankle brace with a flexible splint that includes a stirrup shape fastened to the foot, a middle section formed as a partial helix shape that extends from the outside of the foot over the instep, and an upper end fastened to the leg at a point above the ankle and above the inside of the foot.

11 Claims, 16 Drawing Sheets

ANKLE BRACE

CROSS-REFERENCE TO RELATED APPLICATIONS

This application claims priority to U.S. Provisional Patent App. No. 63/355,997 filed Jun. 27, 2022, the disclosure of which is incorporated herein by reference in its entirety for continuity of disclosure.

FIELD OF THE INVENTION

This invention relates generally to the field of supports for the human body. More particularly, the present invention relates to an improved ankle brace that includes a novel helix-shaped flexible support/splint with enhanced appearance, reduced weight, easier application and removal, and improved performance compared to the prior art.

BACKGROUND OF THE INVENTION

Ankle braces are used by athletes and other persons engaged in vigorous physical activity to try to protect the ankle from injury and also to reduce exacerbation of existing injury. The ankle is one of the most heavily used joints of the body, as it is used in any activity that involves walking or running. The ankle is also a common subject of injury, due to the relatively high levels of stress it must bear. During normal ambulation, in occupations involving physical labor, and especially during strenuous sports, the ankle can undergo abnormal motions as a result of quick changes in direction, fatigue, uneven surfaces, or impacts. These abnormal motions can cause sprains or more serious injuries, including dislocation, stretching, or tearing of the tissues that make up the ankle.

Many prior art ankle braces for athletic use (e.g. the ankle braces taught in U.S. Pat. Nos. 4,878,404 5,814,002 and 7,014,621) combine a flexible jacket or base that envelops the foot and ankle with a closure system (typically shoelaces threaded through eyelets in the base) for securing the ankle brace on the foot and ankle of the wearer. Applying this kind of prior art ankle brace typically requires loosening the shoelaces enough to insert the foot into the base, iteratively tightening the shoelaces, and finally tying the shoelaces. Removal involves reversing the application process. The process of both application and removal of this kind of prior art ankle brace can be cumbersome and time consuming.

Further, this kind of prior art ankle brace is typically worn under athletic footwear, such as football cleats, basketball shoes, or tennis shoes. The shoelace closure system and flexible base in this kind of prior art ankle brace can be bulky, so that it may not fit comfortably into the normal shoes of the user. The materials required for the closure system and base can add weight that slows an athlete down. What is needed is an improved ankle brace that avoids or reduces these problems and provides superior performance compared to the prior art.

SUMMARY OF THE INVENTION

A first embodiment of the invention is an ankle brace having a splint made of flexible sheet material and includes a partial helix shape that extends from the outside sole of the foot upward and rearward over the instep to a point above the ankle when the ankle brace is worn.

A second embodiment of the invention is a splint for use in an ankle brace, where the splint is made of flexible sheet material and includes a partial helix shape that extends from the outside sole of the foot upward and rearward over the instep to a point above the ankle when the ankle brace is worn.

Further objects, features, and advantages of the invention will be apparent from the following detailed description when taken in conjunction with the accompanying drawings.

DETAILED DESCRIPTION OF THE INVENTION

Figure 1L:
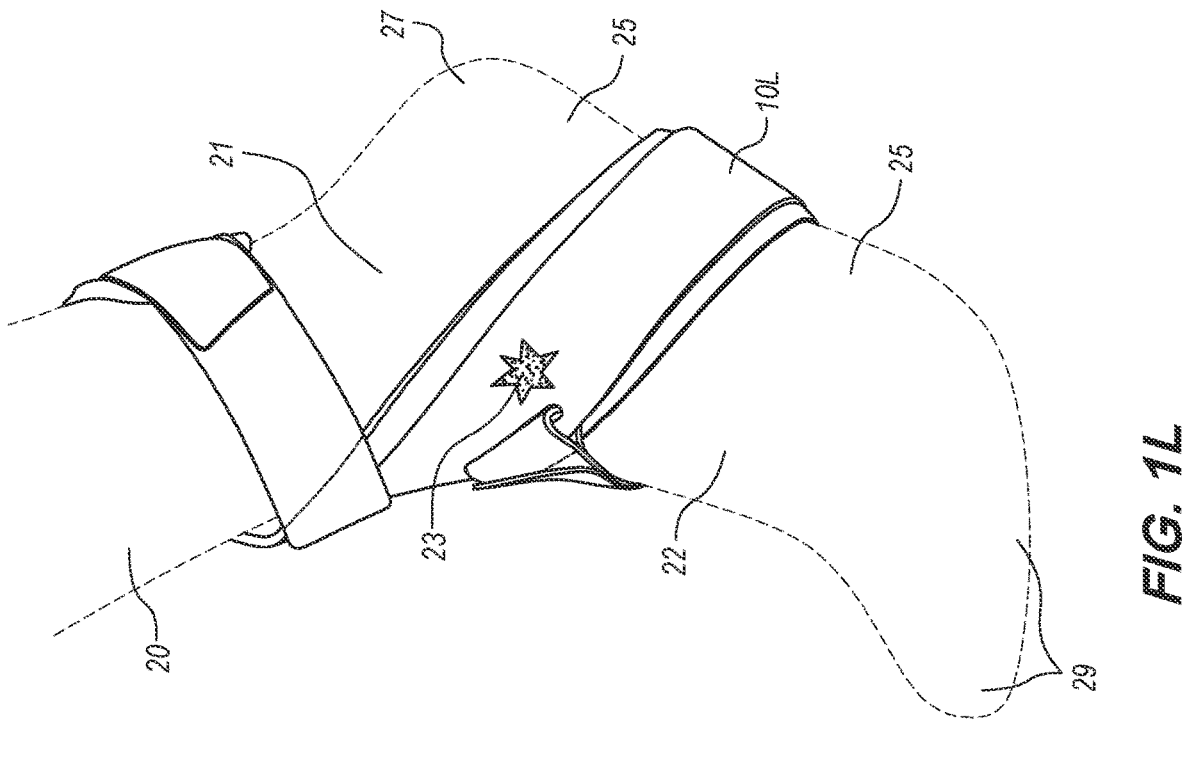
FIGS. 1R and 1L depict front perspective views of right and left foot versions, respectively, of an ankle brace according to the invention as normally applied to the foot and ankle of a person.
Figure 1R:
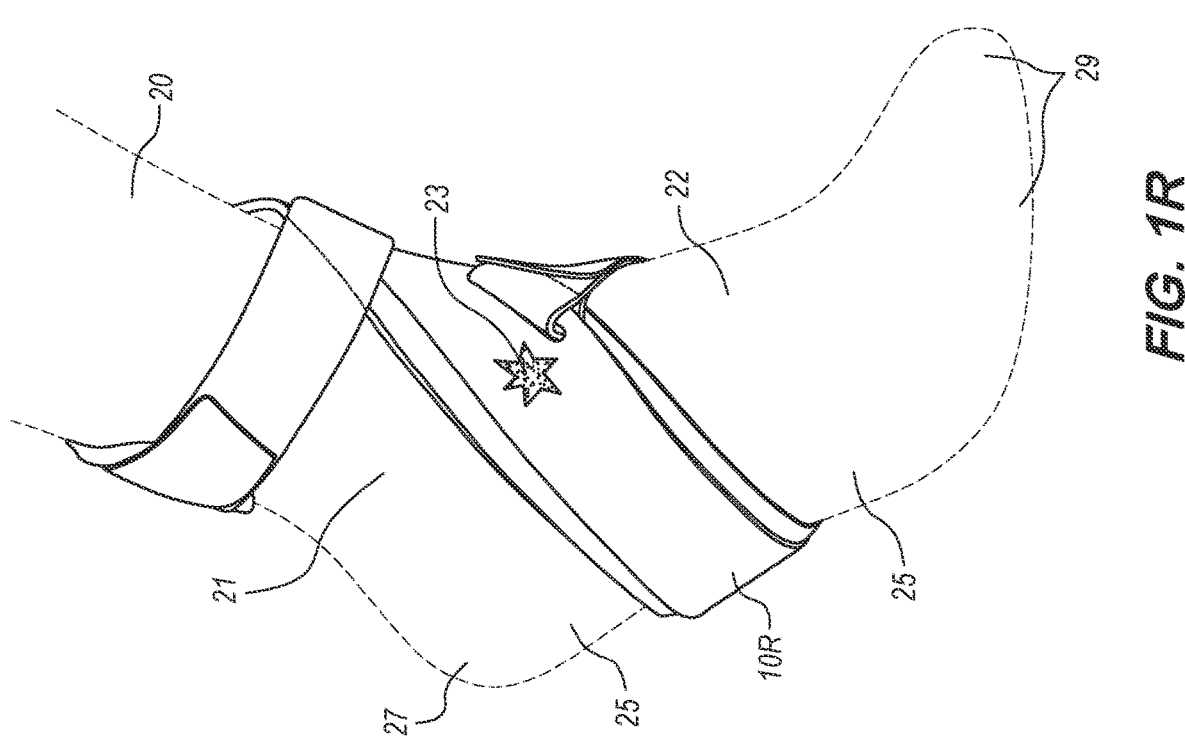
Figures 2L, 2R:
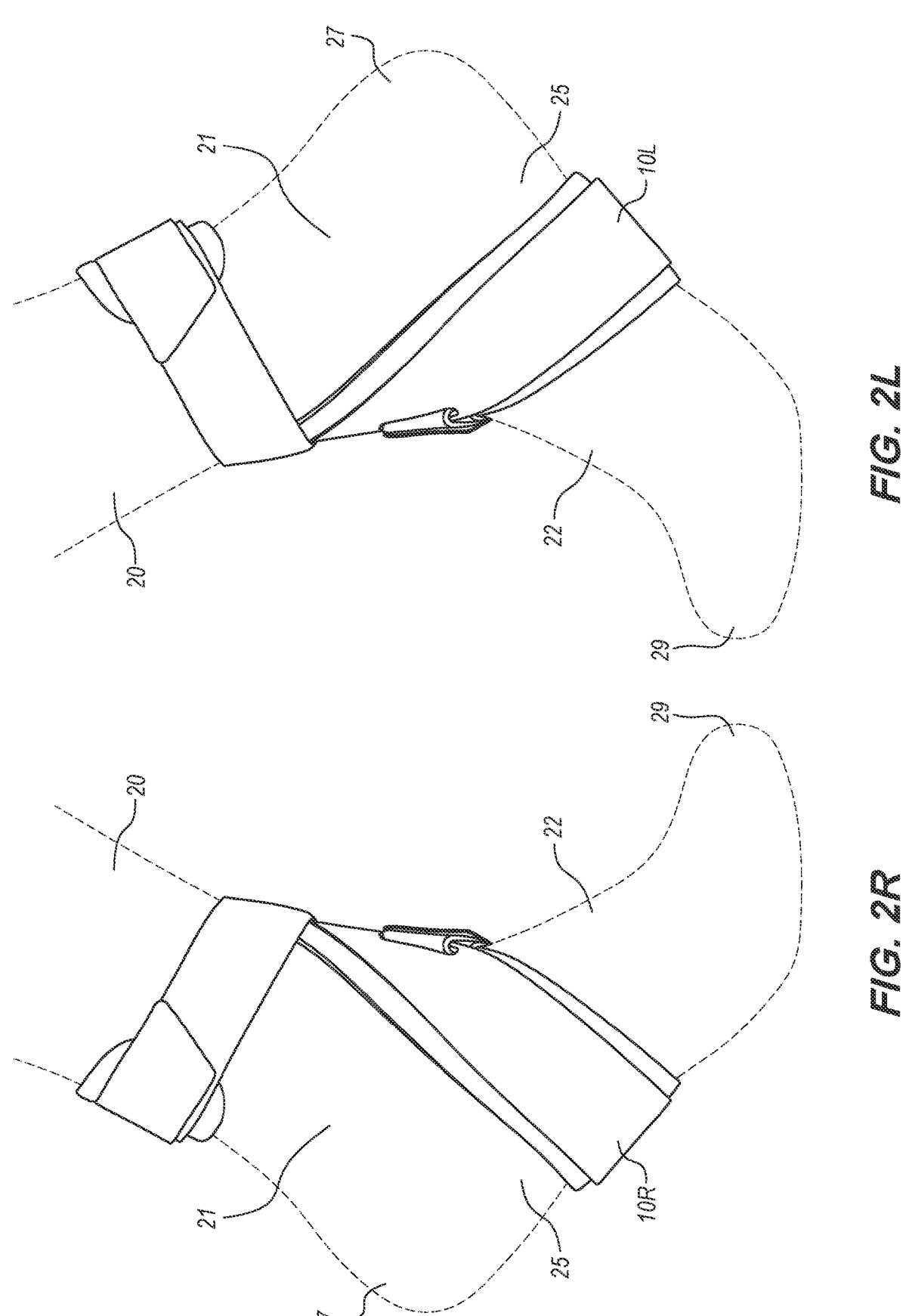
FIGS. 2R and 2L are outside (distal) plan views of the ankle braces of FIGS. 1R and 1L, respectively.
Figures 8L, 8R:
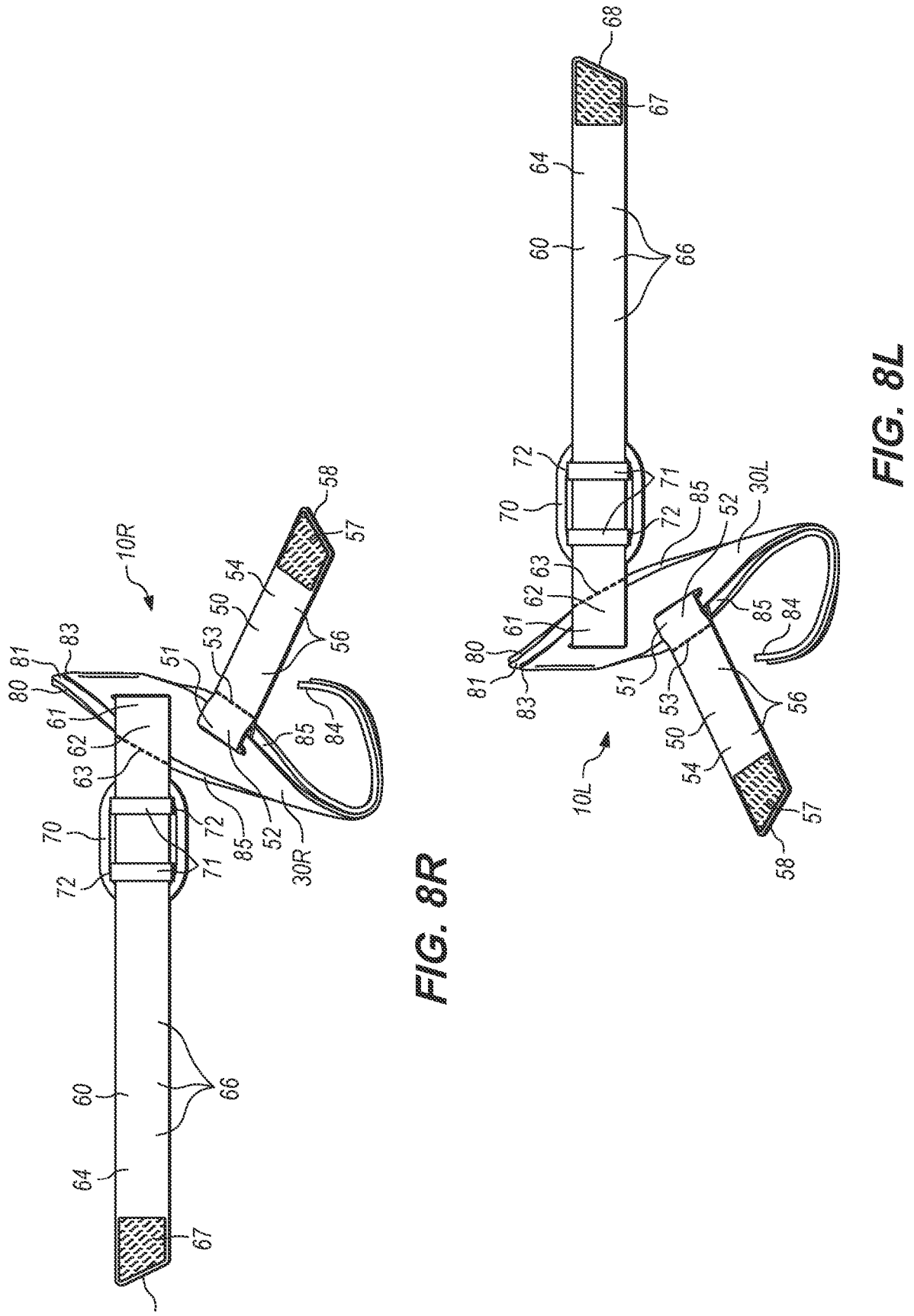
FIGS. 8R and 8L are front plan views of the ankle braces of FIGS. 1R and 1L, respectively, in isolation and with the fastening straps extended to show detail.
Figures 10L, 10R:
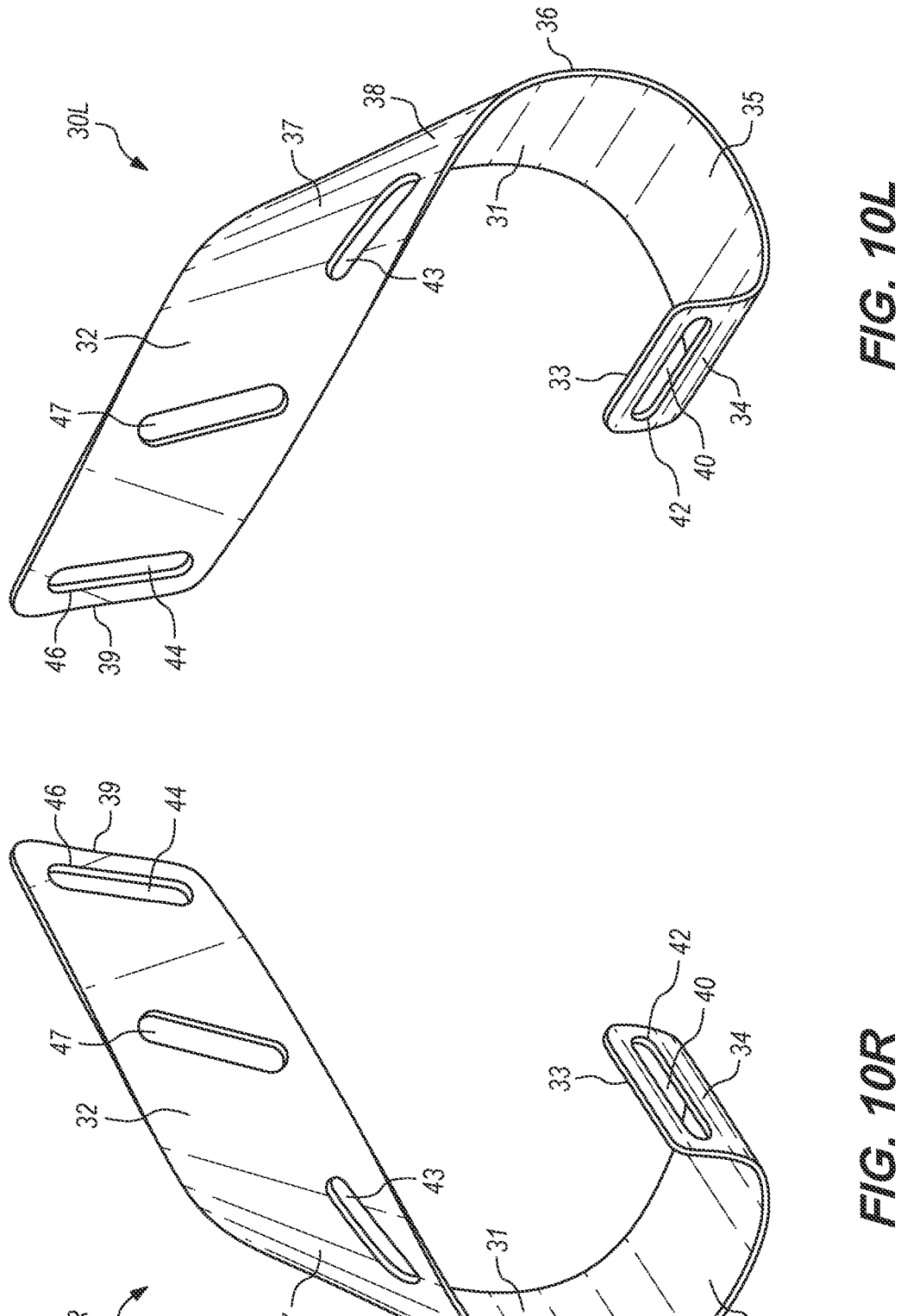
FIGS. 10R and 10L depict front perspective views of right and left foot versions, respectively, of a flexible support for an ankle brace according to the invention.
Figure 11R:
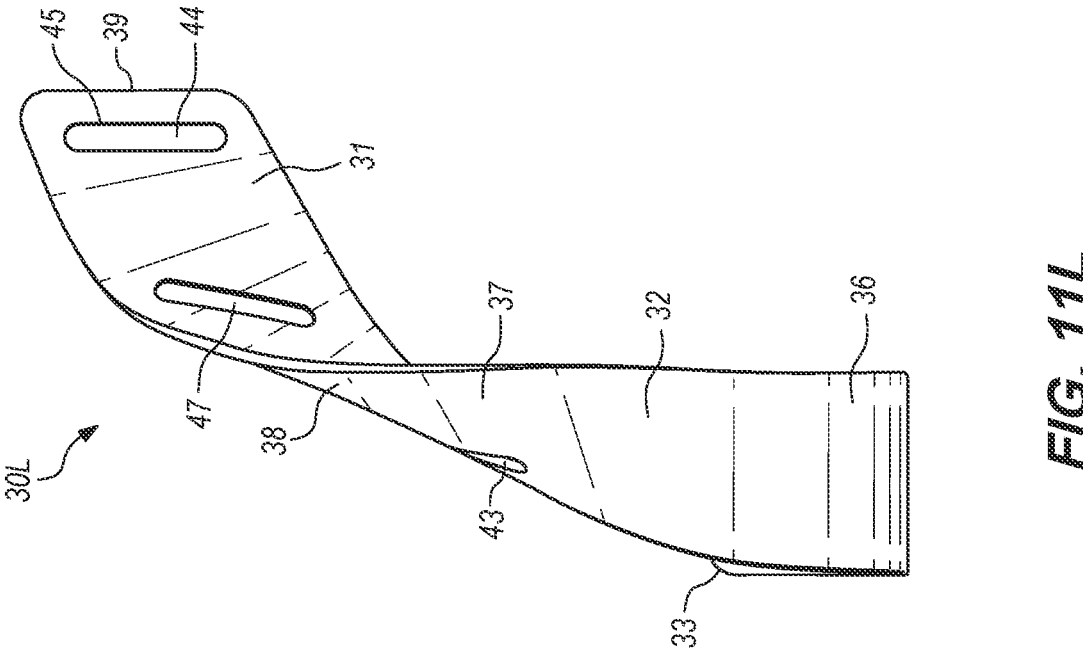
FIGS. 11R and 11L are outside (distal) plan views of the flexible supports of FIGS. 10R and 10L, respectively.
Figure 11L:
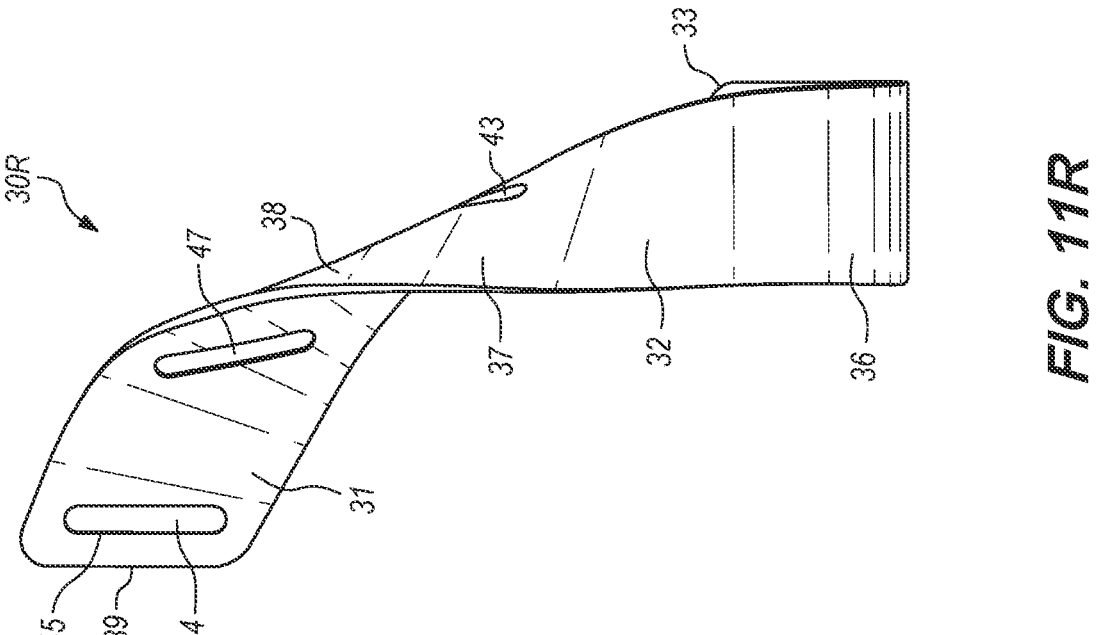
Figure 12L:
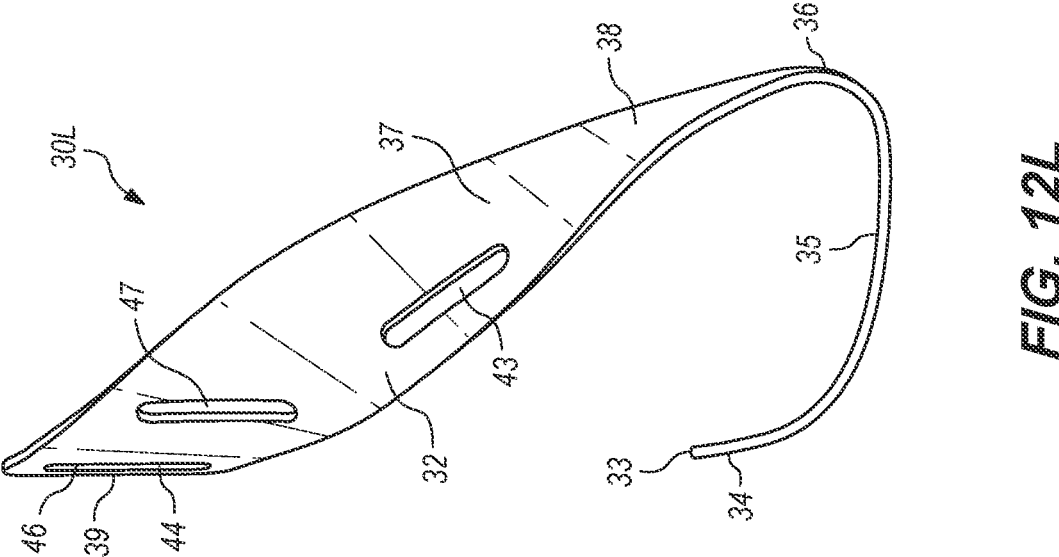
FIGS. 12R and 12L are front plan views of the flexible supports of FIGS. 10R and 10L, respectively.
Figure 12R:
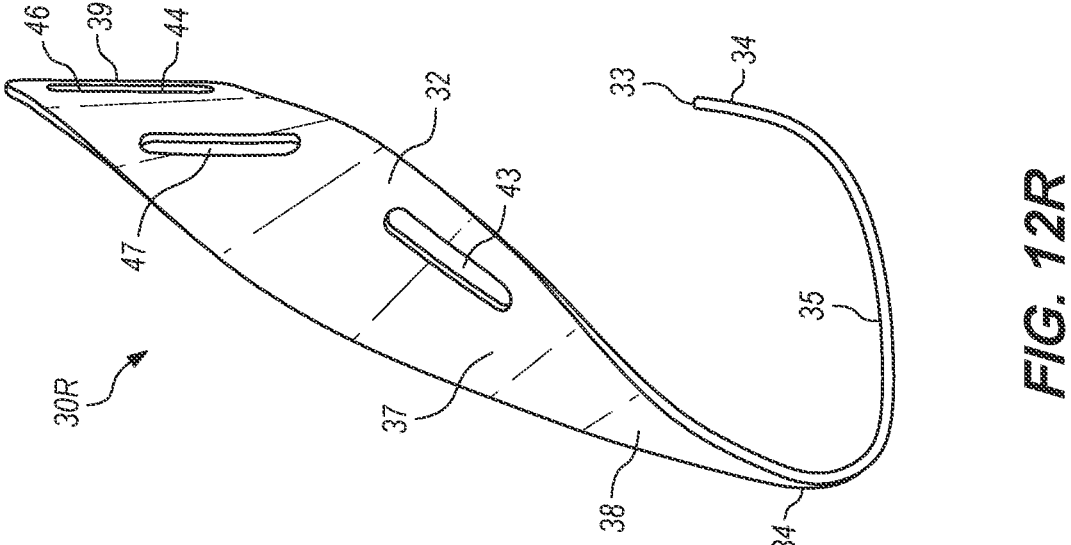
Figures 13L, 13R:
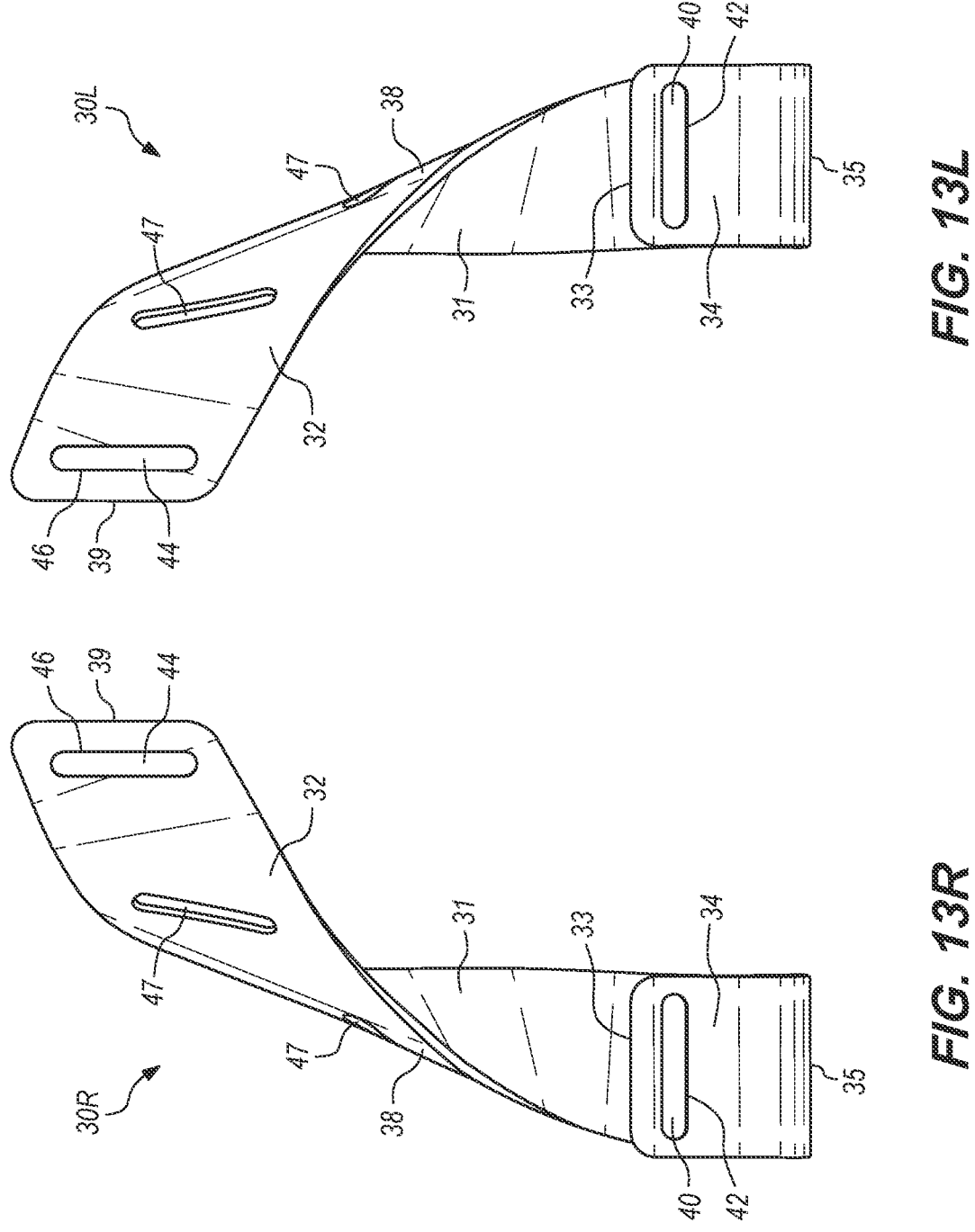
FIGS. 13R and 13L are inside (medial) plan views of the flexible supports of FIGS. 10R and 10L, respectively.
Figure 14R:
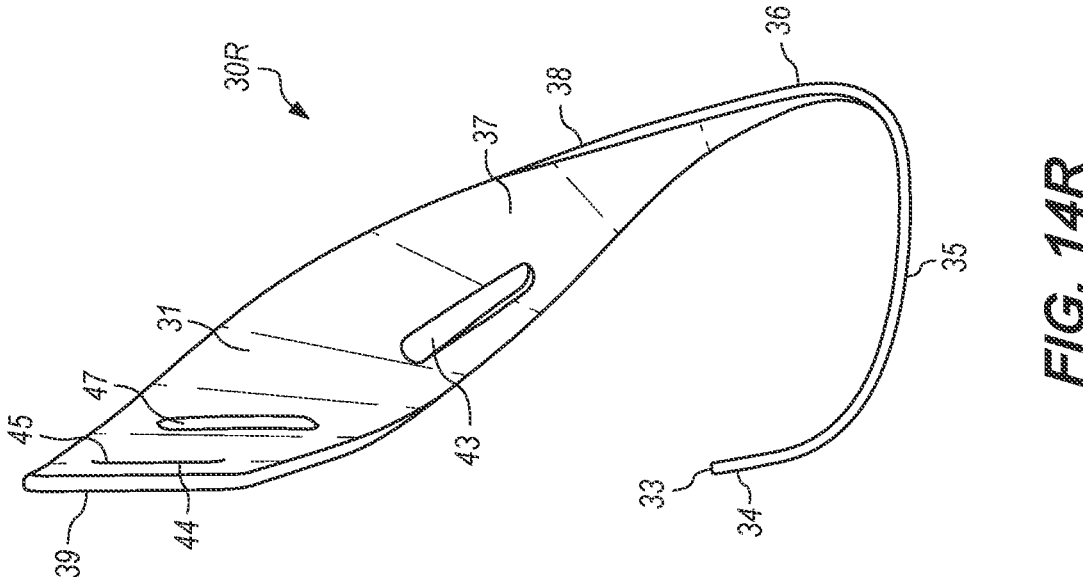
FIGS. 14L and 14R are rear plan views of the flexible supports of FIGS. 10L and 10R, respectively.
Figure 14L:
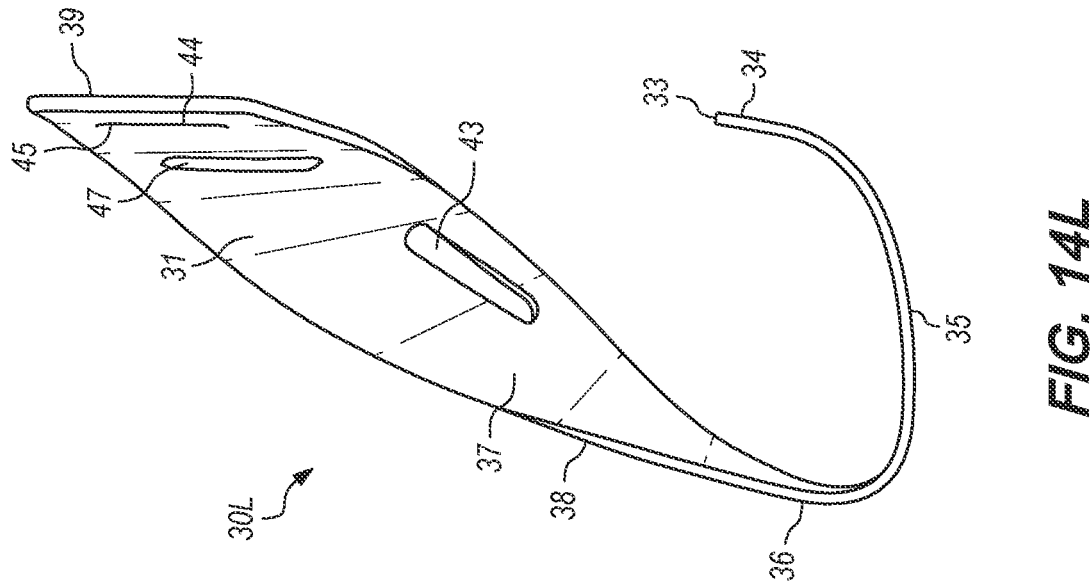
Figure 15L:
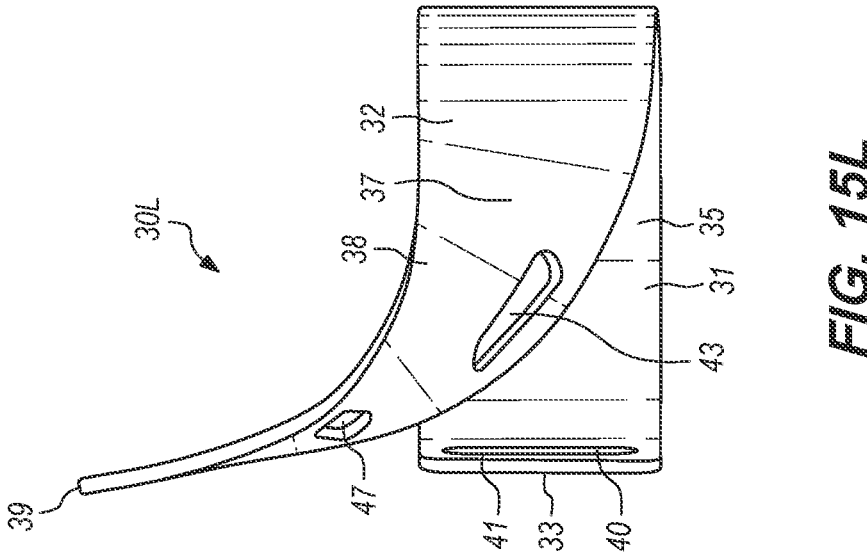
FIGS. 15R and 15L are top plan views of the flexible supports of FIGS. 10R and 10L, respectively.
Figure 15R:
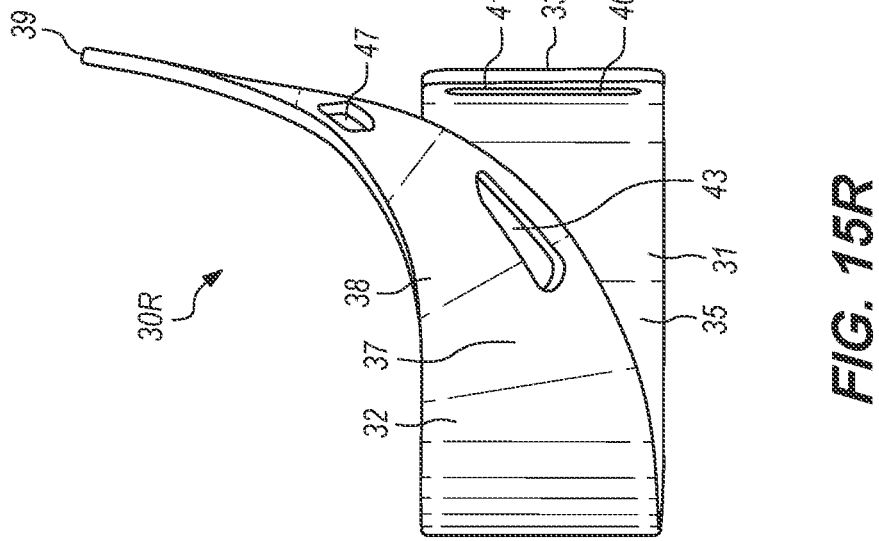
Figure 16L:
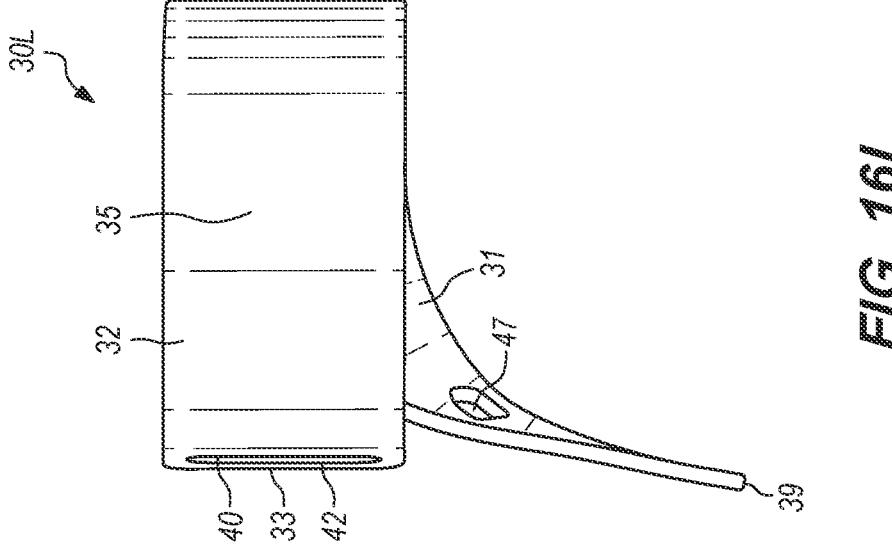
FIGS. 16R and 16L are bottom plan views of the flexible supports of FIGS. 10R and 10L, respectively.
Figure 16R:
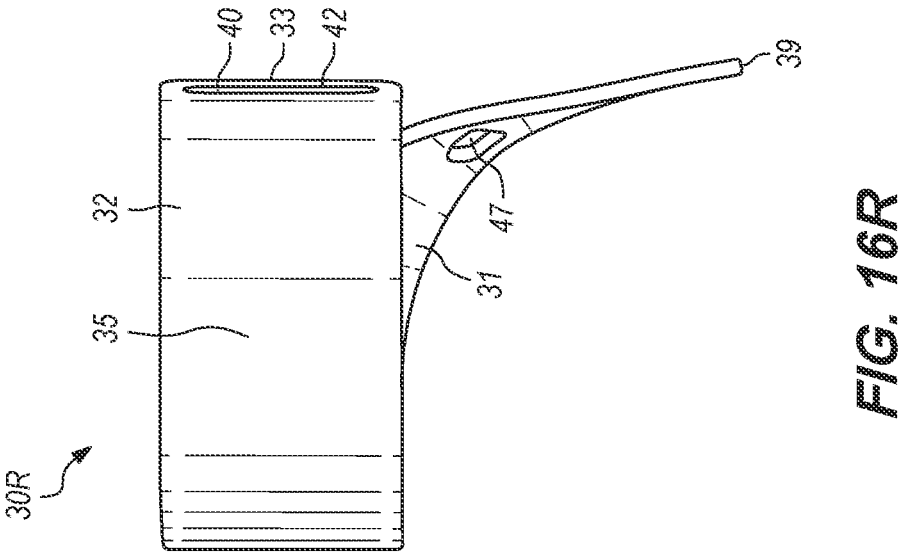

Exemplary ankle braces 10R (right foot version) and 10L (left foot version) according to the invention are shown in the various views of FIGS. 1R/1L-7R/7L applied about the ankle 21 of a person. The ankle braces 10R &10L include flexible supports/splints 30R (right foot version) and 30L (left foot version), respectively, as shown in the various views of FIGS. 10R/10L-16R/16L. The construction of the ankle braces 10R & 10L, and the details of the upper strap and lower strap 50 are perhaps best shown in FIGS. 8R/8L-9R/9L.

The present invention includes apparatus and methods relating to ankle brace 10R used on the right ankle by itself (without ankle brace on the left ankle), ankle brace 10L used on the left ankle by itself (without ankle brace 10R on the right ankle), and also the combination of ankle brace 10R on the right ankle and 10L on the left ankle worn as a matched pair. For brevity the detailed description that follows will forgo L and R indications in the (of left vs right versions) for both the figure numbers themselves and for index numbers used in the figures.

As shown in FIGS. 1-7, the ankle brace 10 is worn by a person about their ankle with an upper strap 60 fastened around the person's lower leg and with a lower strap 50 fastened around the person's foot 22. The person's foot 22 has an instep 23 (the top surface of the middle part of the foot 22 between the toes 29 and the ankle 21) and an arch 24 (the bottom surface of the middle part of the foot 22 between the toes 29 and the heel 27). The foot 22 has a sole 28, an outside (distal) portion 25, and an inside (medial) portion 26.

Exemplary novel splints/supports 30R (right foot version) and 30L (left foot version) according to the inventions are shown in the various views of FIGS. 10-16 for use in the ankle braces 10R and 10L, respectively. The novel flexible splint or support 30 is preferably made as a unitary structure from a single sheet of flexible sheet material formed into the shape disclosed in the figures and description of the present application.

The splint 30 is preferably formed of nylon, however other suitable flexible sheet materials such as metal, graphite or carbon fibers, or plastic could be used. To fit a person with ordinary-sized feet (for example, men's US shoe size 9-11/women's US shoe size 10-12) and ankles, the splint is preferably about 1.5" wide and 13" long end-to-end, with the dimensions adjusted up or down appropriately to fit differently sized people.

The splint 30 has an interior face 31, an exterior face 32, a lower end 33, and an upper end 39. The splint 30 is shaped to have an inside vertical section 34, an arch portion 35, and an outside vertical section 36 that together form a stirrup shape terminating at the lower end 33. From the outside vertical section, the splint 30 has an instep portion 37 and a twist portion 38 that together form a partial helix extending upward and rearward across the instep 23 to an upper end 39 of the splint 30 above the inside (medial) portion 26.

When applied, the inside vertical section 34 of the splint 30 is adjacent the inside (medial) portion 26, the arch portion 35 is adjacent the arch 24, the outside vertical section 36 is adjacent the outside (distal) portion 25, and the stirrup shape (formed by inside vertical section 34, arch portion 35, and outside vertical section 36) is fastened to the person's foot 22 using lower fastening strap 50. From the outside vertical section 36 adjacent the outside (distal) portion 25, the splint 30 has an instep portion 37 and twist portion 38 extending upward and rearward to form a partial helix shape adjacent the instep 23 that ultimately terminates above the ankle and above the inside (medial) portion 26 at the upper end 39 that is fastened to the lower leg 20 using upper fastening strap 60.

The splint 30 has a lower strap fastening slot 40 formed as an aperture between a lower strap fastening slot interior opening 41 on the interior face 31 and a lower strap fastening slot exterior opening 42 on the exterior face 32, and a lower strap attachment slot 43. The splint 30 also has an upper strap attachment slot 47, and an upper strap fastening slot 44 formed as an aperture between an upper strap fastening slot interior opening 45 on the interior face 31 and an upper strap fastening slot exterior opening 46 on the exterior face 32.

Figures 9L, 9R:
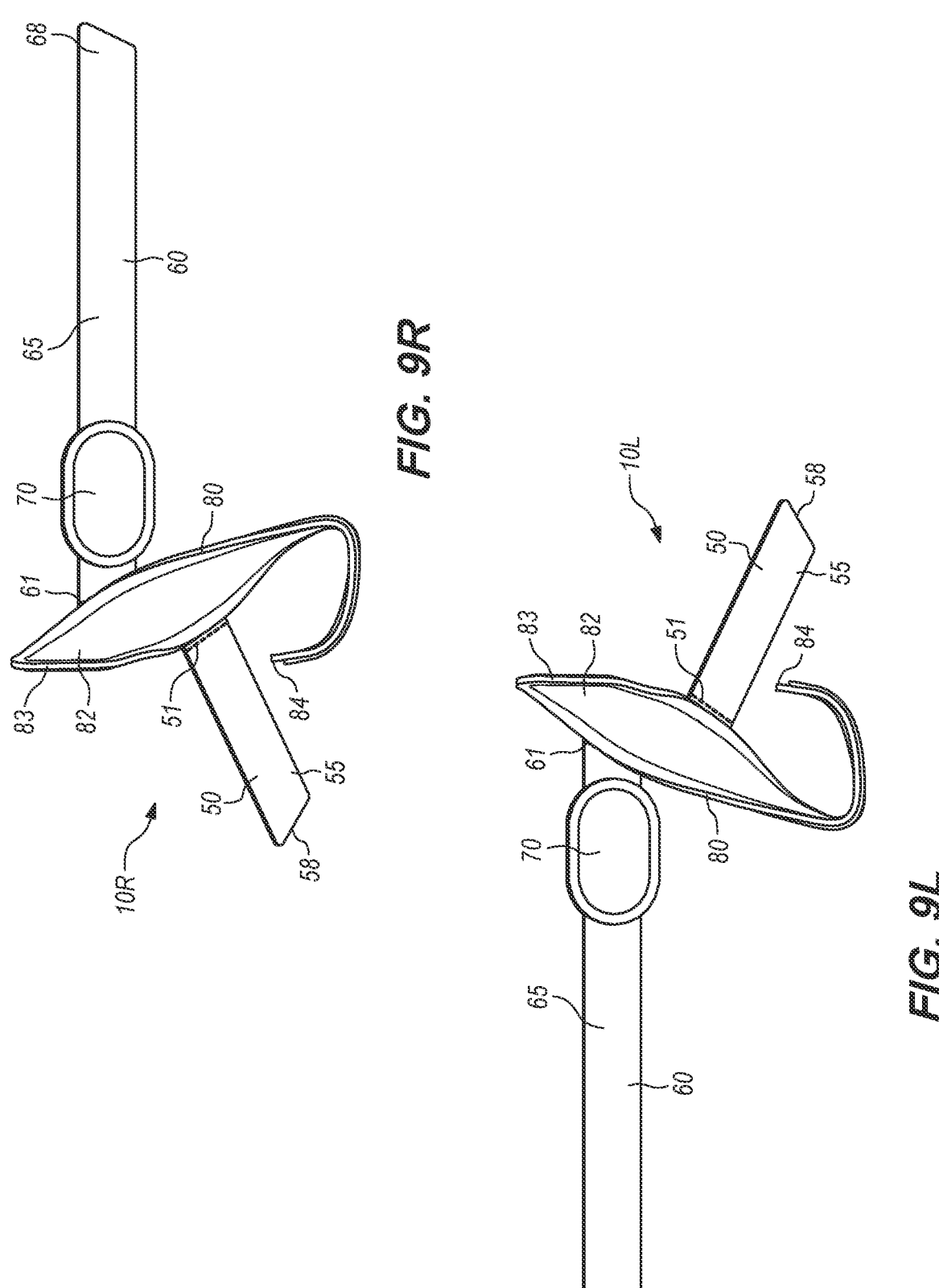
FIGS. 9R and 9L are rear plan views of the ankle braces of FIGS. 1R and 1L, respectively, in isolation and with the fastening straps extended to show detail.

As best shown in FIGS. 8-9, the lower strap 50 has an exterior face 54 and an interior face 55. The lower strap 50 terminates in a fixed end 51 that is permanently attached, for example using an attachment loop 52 formed with stitches

53, to the lower strap attachment slot 43 in the splint 30. The exterior face 54 bears loop material 56 on its surface, except for a hook material patch 57 on the exterior face 54 near the loose (fastening) end 58.

Figures 4L, 4R:
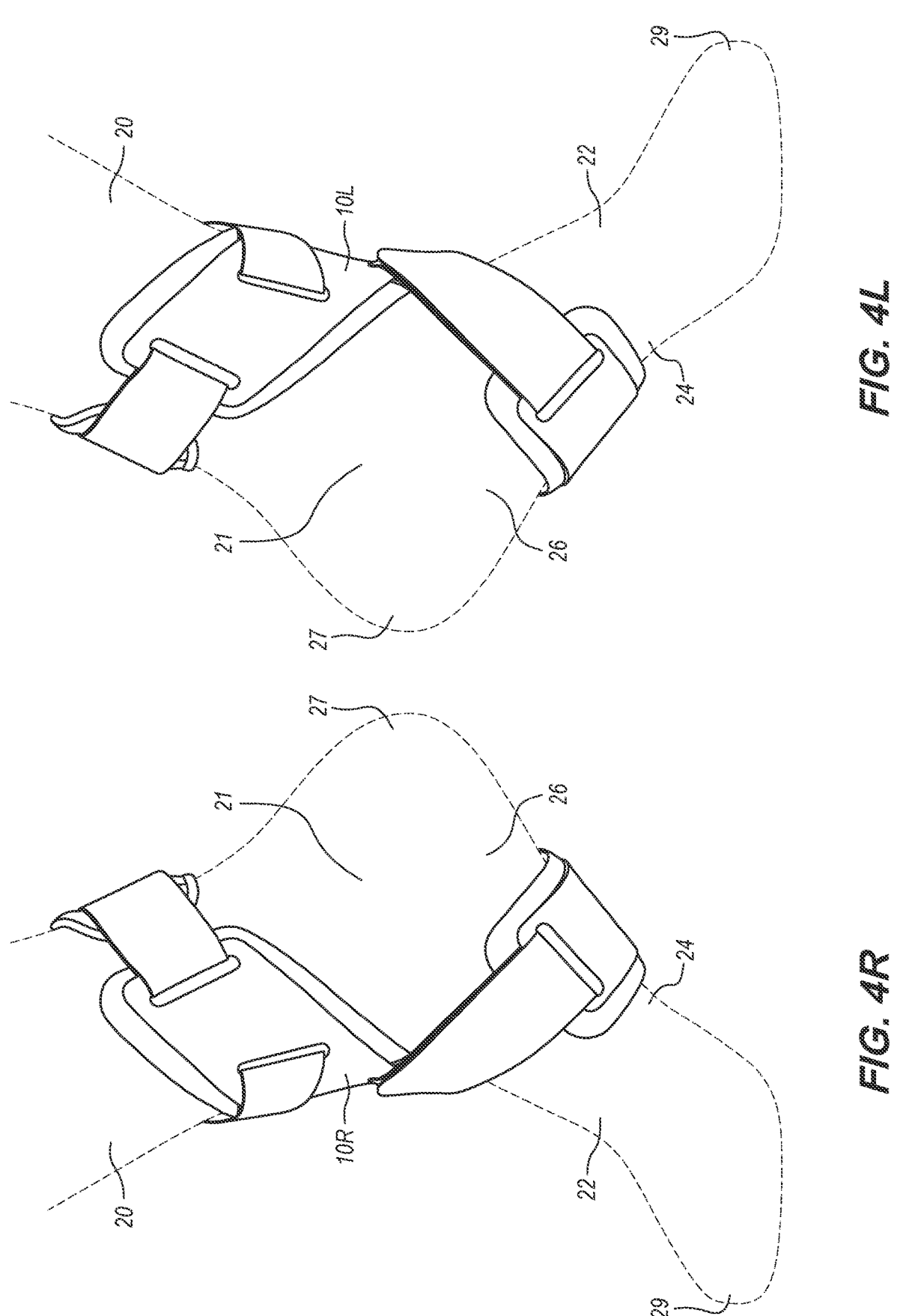
FIGS. 4R and 4L are inside medial plan views of the ankle braces of FIGS. 1R and 1L, respectively.

As perhaps best shown in FIG. 4, to fasten the lower strap 50 about the foot 22, the loose (fastening) end 58 of the lower strap 50 is passed into the interior opening 41 of the lower strap fastening slot 40 and out the exterior opening 42, to loop the lower strap 50 back on itself with the hook material patch 57 pressed against the loop material 56 to form a detachable attachment.

As best shown in FIGS. 8-9, the upper strap 60 has an exterior face 64 and an interior face 65. The upper strap 60 terminates in a fixed end 61 that is permanently attached, for example using an attachment loop 62 formed with stitches 63, to the upper strap attachment slot 47 in the splint 30. The exterior face 64 bears loop material 66 on its surface, except for a hook material patch 67 on the exterior face 64 near the loose (fastening) end 68. The upper strap 60 includes a floating achilles tendon pad 70 loosely connected to the upper strap 60 using retention bands 71 preferably formed of elastic so the position of the pad 70 may be adjusted by sliding the pad 70 back and forth on the strap 60.

Figure 3L:
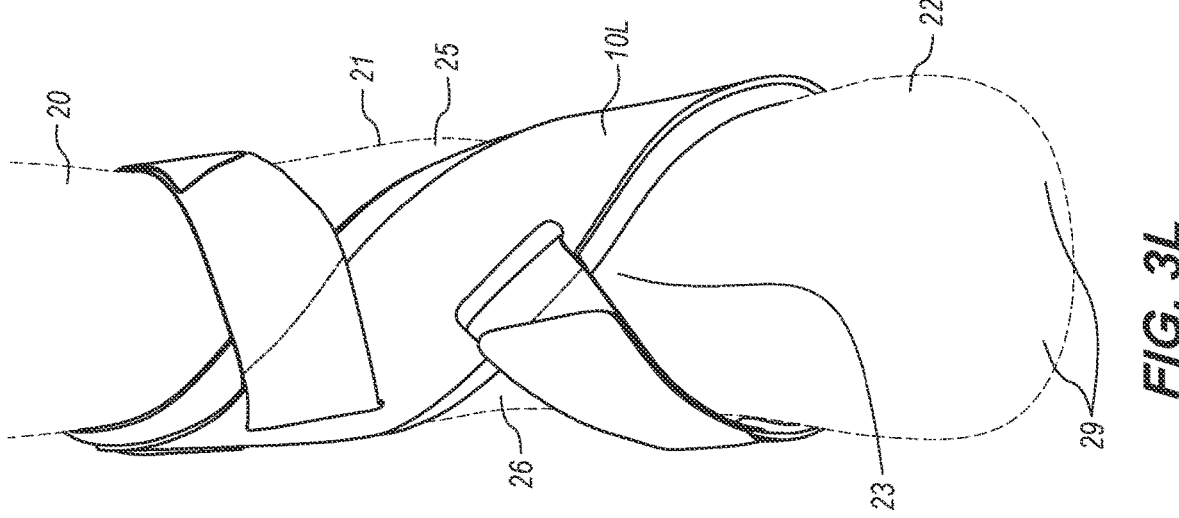
FIGS. 3R and 3L are front plan views of the ankle braces of FIGS. 1R and 1L, respectively.
Figure 3R:
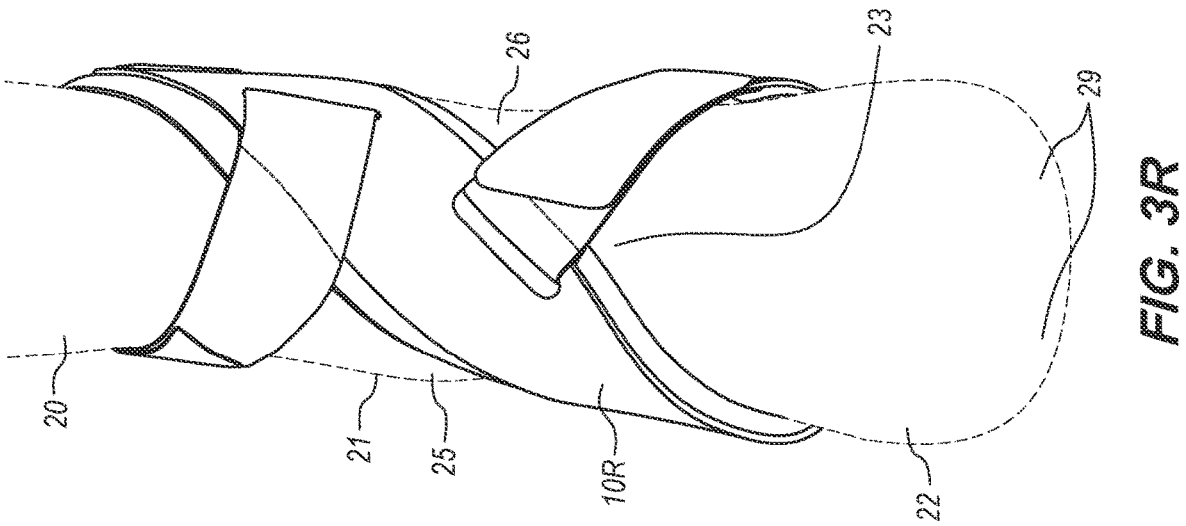
Figures 5L, 5R:
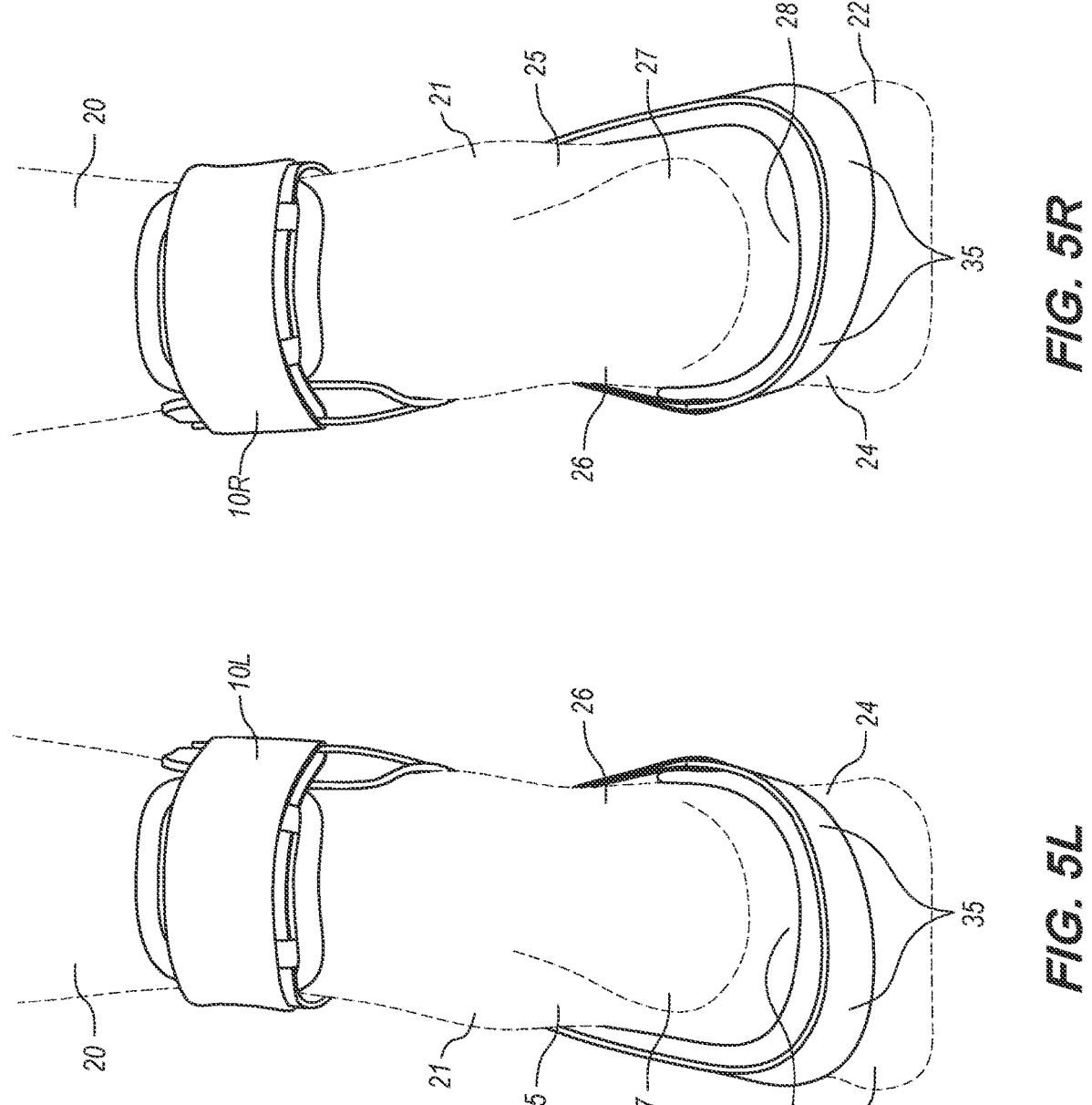
FIGS. 5L and 5R are rear plan views of the ankle braces of FIGS. 1L and 1R, respectively.
Figure 6L:
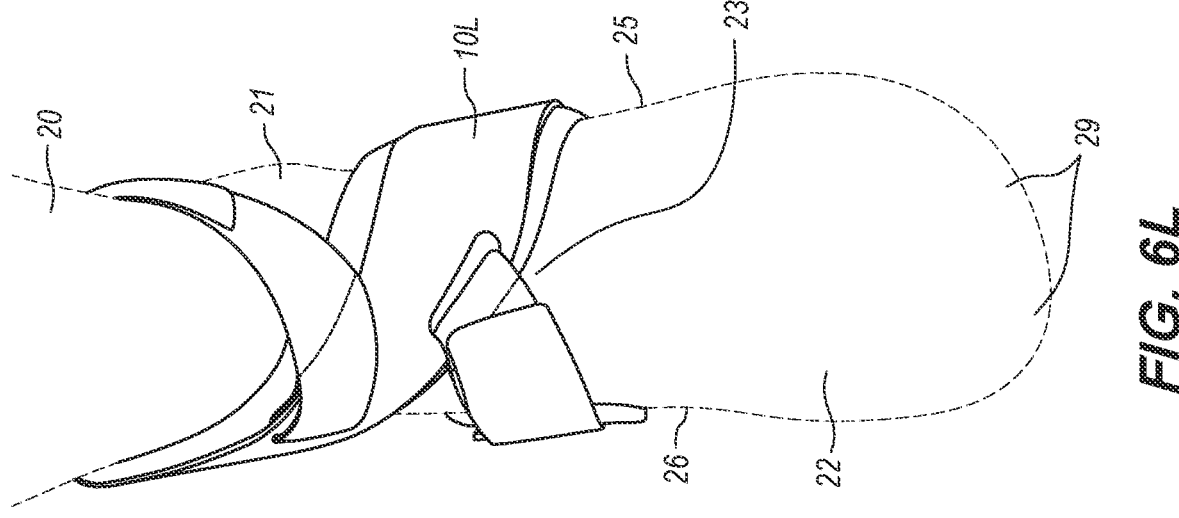
FIGS. 6R and 6L are top plan views of the ankle braces of FIGS. 1R and 1L, respectively.
Figure 6R:
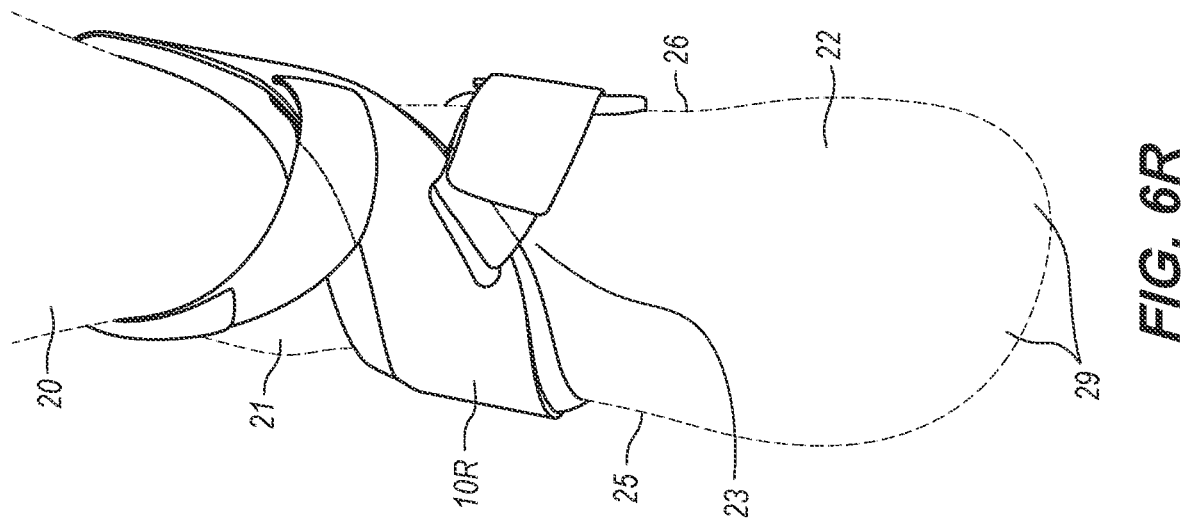
Figure 7L:
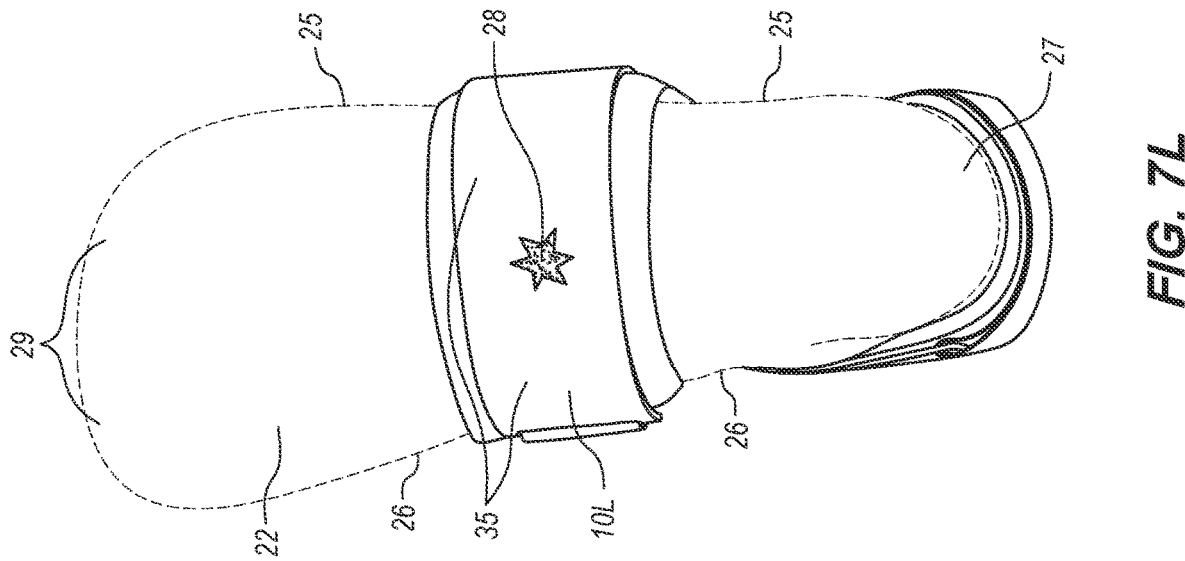
FIGS. 7R and 7L are bottom plan views of the ankle braces of FIGS. 1L and 1R, respectively.
Figure 7R:
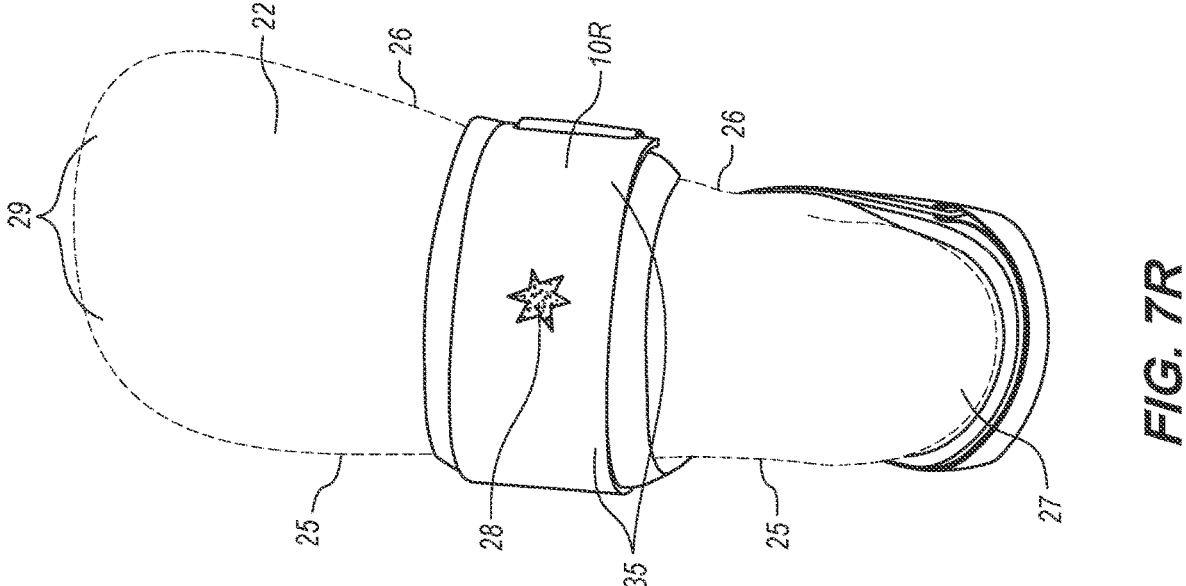

As perhaps best shown in FIG. 3-5, to fasten the upper strap 60 above the ankle 21 and about the lower leg 20, with the achilles tendon pad 70 positioned appropriately, the loose (fastening) end 68 of the upper strap 60 is passed into the interior opening 45 of the upper strap fastening slot 44 and out the exterior opening 46, to loop the upper strap 60 back on itself with the hook material path 67 on the loose (fastening) end pressed against the loop material 66 to form a detachable attachment with the brace fastened on the wearer.

Although stitches are referred to as a preferred method of permanent fastening, for example to form the attachment loop 52 and attachment loop 62, this is not required and other permanent fastening methods could be used such as glue or ultrasonic welding, heat welding, rivets, or other methods. As used in this application and its claims, the term "permanently attached" means permanently fastened together by any such means, including but not limited to permanently fastened together with stitches or sewing.

Although an aperture or slot in the splint may be used to receive the fixed end of a strap, other permanent attachment methods could be used, and the term "slot" as used herein includes any permanent attachment point on the splint. Although hook-and-loop material is used for detachable attachment of the upper and lower straps, other means could be used, such as zippers, buckles, buttons, or closure systems of the kind used on sandwich bags.

The ankle brace 10 of the present invention has several advantages. It has a modern design that is elegant and novel in appearance. It has relatively few components, which reduces weight and bulk compared to prior art braces. The reduced bulk means the ankle brace 10 can have a thinner profile (compared to braces that use a base that covers most of the foot) and fit into an athletes existing shoes better. Application requires fastening only two straps, and ingress/egress is quicker and easier compared to braces that use laces for application. Using the upper strap 60 and lower strap 50, the flexible splint can be adjustably fastened about the foot and about the ankle region to accommodate different people within a range of sizes, although multiple sizes (SM, MD, LG, XL, etc. may be needed to cover substantially all consumers.

It is understood that the invention is not confined to the embodiments set forth herein as illustrative but embraces all such forms thereof that come within the scope of the following claims.

What is claimed is:

1. An ankle brace comprising
   (a) a splint made of flexible sheet material with an interior face and an exterior face, an upper end and a lower end;
   (b) an upper fastening strap for detachably fastening the upper end of the splint above an ankle and about a lower leg of a person, the ankle having an inside (medial) side and an outside (distal) side; and
   (c) a lower fastening strap for detachably fastening the lower end of the splint about a foot of the person, the foot having an inside (medial) portion, a sole, an outside (distal) portion, and an instep;
   wherein the lower end of the splint includes an inside vertical section shaped to fit the inside (medial) portion and wherein the lower end is configured to terminate below the inside (medial) side of the ankle, a sole section shaped to fit the sole of the foot, and an outside vertical section shaped to fit the outside (distal) portion that together form a stirrup shape;
   and wherein the splint has an instep portion and a twist portion that together form a partial helix configured to extend upward and rearward across the instep to the upper end and wherein the upper end is configured to terminate above the inside (medial) side of the ankle.

2. The ankle brace of claim 1 adapted for the left foot, wherein the outside vertical section is on the right side of the splint and the inside vertical section is on the left side of the splint, when viewed from the front.

3. The ankle brace of claim 1 adapted for the right foot, wherein the outside vertical section is on the left side of the splint and the inside vertical section is on the right side of the splint, when viewed from the front.

4. The ankle brace of claim 1 wherein the splint includes a lower strap attachment slot in the instep portion, and the lower fastening strap is permanently attached to the splint using a sewn loop through the lower strap attachment slot.

5. The ankle brace of claim 4 wherein the splint includes a lower strap fastening slot, and the lower fastening strap bears a loop material and bears a hook material.

6. The ankle brace of claim 1 wherein the splint includes an upper strap attachment slot, and the upper fastening strap is permanently attached to the splint using a sewn loop through the upper strap attachment slot.

7. The ankle brace of claim 6 wherein the splint includes an upper strap fastening slot, and the upper fastening strap bears a loop material and bears a hook material.

8. A splint for an ankle brace made from flexible sheet material,
   generally rectangular in shape with a length and a width, an interior face and an exterior face, an upper end and a lower end, and an outside (distal) side and an inside (medial) side;
   wherein the lower end of the splint includes an outside vertical section, a sole section, and an inside vertical section that form a stirrup shape, wherein the inside vertical section includes a lower strap fastening slot;
   wherein the splint includes an instep portion and a twist portion that together form a partial helix shape extending from the outside vertical section to the upper end on the inside (medial) side, and wherein the lower end and the upper end are both on the inside (medial) side; wherein the instep portion includes a lower strap attachment slot; and
   wherein the upper end of the splint includes an upper strap fastening slot and an upper strap attachment slot.

9. The splint of claim 8 adapted for the left foot, wherein the outside vertical section is on the right side of the splint and the inside vertical section is on the left side of the splint, when viewed from the front.

10. The splint of claim 8 adapted for the right foot, wherein the outside vertical section is on the left side of the splint and the inside vertical section is on the right side of the splint, when viewed from the front.

11. The splint of claim 8 wherein the width is between 1" and 2", and the length is between 11" and 15".

* * * * *